US012569409B2

(12) United States Patent
Ishiwata et al.

(10) Patent No.: US 12,569,409 B2
(45) Date of Patent: Mar. 10, 2026

(54) DENTAL POLYMERIZABLE COMPOSITION

(71) Applicant: GC Corporation, Shizuoka (JP)

(72) Inventors: Ken Ishiwata, Tokyo (JP); Keita Sato, Tokyo (JP); Shogo Murakami, Tokyo (JP); Yusuke Shimada, Tokyo (JP)

(73) Assignee: GC Corporation, Shizuoka (JP)

( * ) Notice: Subject to any disclaimer, the term of this patent is extended or adjusted under 35 U.S.C. 154(b) by 289 days.

(21) Appl. No.: 18/552,268

(22) PCT Filed: Feb. 2, 2022

(86) PCT No.: PCT/JP2022/004136
§ 371 (c)(1),
(2) Date: Sep. 25, 2023

(87) PCT Pub. No.: WO2022/209269
PCT Pub. Date: Oct. 6, 2022

(65) Prior Publication Data
US 2024/0189195 A1     Jun. 13, 2024

(30) Foreign Application Priority Data

Mar. 31, 2021     (JP) ................................. 2021-062368

(51) Int. Cl.
| | |
|---|---|
| *A61K 6/30* | (2020.01) |
| *A61K 6/16* | (2020.01) |
| *A61K 6/77* | (2020.01) |
| *A61K 6/836* | (2020.01) |
| *A61K 6/887* | (2020.01) |

(52) U.S. Cl.
CPC .................. *A61K 6/30* (2020.01); *A61K 6/16* (2020.01); *A61K 6/77* (2020.01); *A61K 6/836* (2020.01); *A61K 6/887* (2020.01)

(58) Field of Classification Search
CPC . A61K 6/30; A61K 6/77; A61K 6/887; A61K 6/836; A61K 6/16
See application file for complete search history.

(56) References Cited

U.S. PATENT DOCUMENTS

| | | | | |
|---|---|---|---|---|
| 4,714,721 A | * | 12/1987 | Franek | A61L 24/0089 523/113 |
| 5,204,398 A | * | 4/1993 | Cohen | A61K 6/887 524/430 |
| 5,883,153 A | * | 3/1999 | Roberts | A61K 6/20 524/916 |
| 6,583,197 B1 | * | 6/2003 | Wada | A61K 6/30 522/182 |
| 10,301,212 B2 | | 5/2019 | Dahlmann et al. | |
| 2006/0194172 A1 | * | 8/2006 | Loveridge | A61K 6/30 106/35 |
| 2008/0057000 A1 | | 3/2008 | Loveridge | |
| 2009/0048366 A1 | * | 2/2009 | Torii | A61K 6/77 523/118 |
| 2009/0317772 A1 | * | 12/2009 | Rusin | A61K 6/30 501/48 |
| 2012/0059083 A1 | | 3/2012 | Tokui et al. | |
| 2022/0339079 A1 | | 10/2022 | Sato et al. | |
| 2024/0189195 A1 | * | 6/2024 | Ishiwata | A61K 6/16 |

FOREIGN PATENT DOCUMENTS

| | | |
|---|---|---|
| DE | 102006045628 | 4/2008 |
| JP | H06-72028 | 9/1994 |
| JP | 3497508 | 2/2004 |
| JP | 2005-247820 | 9/2005 |
| JP | 2008-520565 | 6/2008 |
| JP | 2012-051856 | 3/2012 |
| WO | 2007/088628 | 8/2007 |
| WO | 2021/049268 | 3/2021 |

OTHER PUBLICATIONS

Optics Mag, https://opticsmag.com/what-is-the-refractive-index-of-glass/ (Year: 2025).*
International Search Report for PCT/JP2022/004136 mailed on Mar. 29, 2022.

* cited by examiner

*Primary Examiner* — Ralph A Lewis

(74) *Attorney, Agent, or Firm* — IPUSA, PLLC

(57) ABSTRACT

A dental polymerizable composition includes a (meth)acrylate compound; and a glass. The glass includes gadolinium.

6 Claims, No Drawings

DENTAL POLYMERIZABLE COMPOSITION

TECHNICAL FIELD

The disclosures herein generally relate to a dental polymerizable composition.

BACKGROUND ART

As an example of a dental polymerizable composition, a dental polymerizable composition that includes a first agent including a (meth)acrylate, a thiourea derivative, and a vanadium compound, and a second agent including a (meth) acrylate and an organic peroxide is known (see, for example, Patent Literature 1).

CITATION LIST

Patent Literature

PTL 1: Japanese Unexamined Patent Application Publication No. 2012-051856

SUMMARY OF INVENTION

Technical Problem

However, a dental polymerizable composition having higher X-ray contrast (X-ray impermeability) is desired. As a method of improving the X-ray contrast, there is a method of containing barium glass. However, when a large amount of barium glass is blended, the composition becomes hard, and operability is deteriorated.

An object of the present invention is to provide a dental polymerizable composition having high X-ray contrast without deteriorating operability.

Solution to Problem

According to one aspect of the present disclosure, a dental polymerizable composition including: a (meth)acrylate compound; and a glass; wherein the glass includes gadolinium, is provided.

Advantageous Effects of Invention

According to one aspect of the present disclosure, a dental polymerizable composition having high X-ray contrast without deteriorating operability, can be provided.

DESCRIPTION OF EMBODIMENTS

In the following, embodiments of the present invention will be described in detail.

A dental polymerizable composition according to the present embodiment includes a (meth)acrylate compound and glass. As used herein, a polymerizable composition refers to a composition that has a function of polymerizing.

The (meth)acrylate compound included in the dental polymerizable composition refers to a monomer, an oligomer, or a prepolymer of (meth)acrylate having one or more (meth)acryloyloxy groups. As used herein, (meth) acrylate refers to acrylate and/or methacrylate.

(Meth)acrylate is not particularly limited. For example, (meth)acrylate may be (meth)acrylate having an acid group, or (meth)acrylate having no acid group, or both.

The (meth)acrylate having an acid group may have multiple acid groups.

For the (meth)acrylate having an acid group, acid chlorides, alkali metal salts, amine salts, and the like of the (meth)acrylate having an acid group may be used.

Examples of (meth)acrylates having an acid group include (meth)acrylates having a phosphate group, (meth)acrylates having a pyrophosphate group, (meth)acrylates having a thiophosphate group, (meth)acrylates having a carboxyl group, (meth)acrylates having a sulfonic acid group, (meth) acrylates having a phosphonic acid group, and the like.

Examples of (meth)acrylates having a phosphate group include 2-(meth)acryloyloxyethyldihydrogenphosphate, bis [2-(meth)acryloyloxyethyl]hydrogenphosphate, 2-(meth) acryloyloxyethylphenyl hydrogenphosphate, 6-(meth)acryloyloxyhexyldihydrogenphosphate, 6-(meth)acryloyloxy-hexylphenyl hydrogenphosphate, 10-(meth) acryloyloxydecyldihydrogenphosphate, 1,3-di(meth) acryloylpropan-2-dihydrogenphosphate, 1,3-di(meth) acryloylpropan-2-phenylhydrogenphosphate, bis [5-{2-(meth)acryloyloxyethoxycarbonyl}heptyl] hydrogenphosphate, and the like. Among these, 10-methacryloyloxydecyldihydrogenphosphate is preferred in terms of the adhesiveness of the dental polymerizable composition.

Examples of (meth)acrylates having a pyrophosphate group include bis(2-(meth)acryloyloxyethyl) pyrophosphate, bis(4-(meth)acryloyloxybutyl) pyrophosphate, bis(6-(meth)acryloyloxyhexyl) pyrophosphate, bis(8-(meth)acryloyloxyoctyl) pyrophosphate, bis(10-(meth) acryloyloxydecyl) pyrophosphate, and the like.

Examples of (meth)acrylates having a thiophosphate group include 2-(meth)acryloyloxyethyldihydrogenthiophosphate, 3-(meth)acryloyloxypropyldihydrogenthiophosphate, 4-(meth)acryloyloxybutyldihydrogenthiophosphate, 5-(meth)acryloyloxypentyldihydrogenthiophosphate, 6-(meth)acryloyloxyhexyldihydrogenthiophosphate, 7-(meth)acryloyloxyheptyldihydrogenthiophosphate, 8-(meth)acryloyloxyoctyldihydrogenthiophosphate, 9-(meth)acryloyloxynonyldihydrogenthiophosphate, 10-(meth)acryloyloxydecyldihydrogenthiophosphate, 11-(meth)acryloyloxyundecyldihydrogenthiophosphate, 12-(meth)acryloyloxydodecyldihydrogenthiophosphate, 13-(meth)acryloyloxytridecyldihydrogenthiophosphate, 14-(meth)acryloyloxytetradecyldihydrogenthiophosphate, 15-(meth)acryloyloxypentadecyldihydrogenthiophosphate, 16-(meth)acryloyloxyhexadecyldihydrogenthiophosphate, 17-(meth)acryloyloxyheptadecyldihydrogenthiophosphate, 18-(meth)acryloyloxyoctadecyldihydrogenthiophosphate, 19-(meth)acryloyloxynonadecyldihydrogenthiophosphate, 20-(meth)acryloyloxyicosyldihydrogenthiophosphate, and the like.

Examples of (meth)acrylates having a carboxyl group include 2-methacryloyloxyethyl succinic acid, 4-(meth) acryloyloxyethyl trimellitic acid, 4-(meth)acryloyloxyethyl trimellitic anhydride, 4-(meth)acryloyloxydecyl trimellitic acid, 4-(meth)acryloyloxydecyl trimellitic anhydride, 11-(meth)acryloyloxy-1,1-undecanedicarboxylic acid, 1,4-di (meth)acryloyloxy pyromellitic acid, 2-(meth)acryloyloxy-ethylmaleic acid, 2-(meth)acryloyloxyethyl phthalic acid, 2-(meth)acryloyloxyethyl hexahydrophthalic acid, and the like. Among these, 2-methacryloyloxyethyl succinic acid is preferred in terms of the adhesiveness of the dental polymerizable composition.

Examples of (meth)acrylates having a sulfonic acid group include 2-(meth)acrylamide-2-methylpropanesulfonic acid, styrenesulfonic acid, 2-sulfoethyl(meth)acrylate, and the like.

Examples of (meth)acrylates having a phosphonic acid group include 2-(meth)acryloyloxyethylphenylphosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, 10-(meth)acryloyloxydecyl-3-phosphonoacetate, and the like.

The (meth)acrylates having an acid group described above may be used alone, or two or more (meth)acrylates may be used in combination.

Among the (meth)acrylates having an acid group described above, the (meth)acrylate having a phosphate group or carboxyl group is preferred in terms of the solubility of the smear layer and the decalcification property on the tooth surface, and, in particular, the adhesiveness to the enamel, of the dental polymerizable composition.

The content of the (meth)acrylate having an acid group in the dental polymerizable composition is not particularly limited. For example, the content may be 0.1% by mass or more and 20% by mass or less, preferably 0.1% by mass or more and 15% by mass or less, and more preferably 0.1% by mass or more and 10% by mass or less.

When the content of the (meth)acrylate having an acid group in the dental polymerizable composition is 0.1% by mass or more, the adhesiveness to the tooth of the dental polymerizable composition is further improved. When the content is 20% by mass or less, the curability of the dental polymerizable composition is improved.

Examples of (meth)acrylates having no acid group include methyl (meth)acrylate, ethyl (meth)acrylate, isopropyl (meth)acrylate, n-butyl (meth)acrylate, isobutyl (meth) acrylate, hydroxypropyl (meth)acrylate, tetrahydrofurfuryl (meth)acrylate, glycidyl (meth)acrylate, 2-hydroxyethyl (meth)acrylate, 2-hydroxypropyl (meth)acrylate, 3-hydroxypropyl (meth)acrylate, 2-methoxyethyl (meth)acrylate, 2-ethoxyethyl (meth)acrylate, 2-methylhexyl (meth) acrylate, 2-ethylhexyl (meth)acrylate, benzyl (meth) acrylate, 2-hydroxy-1,3-di(meth)acryloyloxypropane, ethylene glycol di(meth)acrylate, diethylene glycol di(meth) acrylate, triethylene glycol di(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth)acrylate, trimethylolpropane tri (meth)acrylate, trimethylolethane tri(meth)acrylate, pentaerythritol tri(meth)acrylate, trimethylolmethane tri (meth)acrylate, pentaerythritol tetra(meth)acrylate, polybutylene glycol di(meth)acrylate, bisphenol A diglycidyl (meth)acrylate, di-2-(meth)acryloyloxyethyl-2,2,4-trimethylhexamethylene dicarbamate, 1,3,5-Tris [1,3-bis {(meth) acryloyloxy}-2-propoxycarbonylaminohexane]-1,3,5-(1H, 3H, 5H)triazine-2,4,6-trione, 2,2-bis [4-(3-(meth)acryloyloxy-2-hydroxypropyl)phenyl]propane, N, N'-(2,2,4-trimethylhexamethylene)bis [2-(aminocarboxy) propane-1,3-diol]tetramethacrylate, and the like.

The (meth)acrylates having no acid group may be used alone, or two or more (meth)acrylates may be used in combination.

Among the (meth)acrylates having no acid group described above, di-2-(meth)acryloyloxyethyl-2,2,4-trimethylhexamethylene dicarbamate and 2-hydroxy-1,3-di (meth)acryloyloxypropane are preferred in terms of improving the mechanical strength of the cured product of the dental polymerizable composition.

The content of the (meth)acrylate having no acid group in the dental polymerizable composition may be 10% by mass or more and 95% by mass or less, preferably 13% by mass or more and 90% by mass or less, and further preferably 15% by mass or more and 80% by mass or less.

When the content of the (meth)acrylate having no acid group in the dental polymerizable composition is 10% by mass or more, the operability of the dental polymerizable composition is improved. When the content of the (meth) acrylate having no acid group in the dental polymerizable composition is 95% by mass or less, the mechanical strength of the crude product of the dental polymerizable composition is improved.

The glass contained in the dental polymerizable composition includes gadolinium. Gadolinium is a rare earth element in which the 4f orbital containing up to 14 electrons is occupied by 7 electrons, which is half the number of electrons that can be occupied, and all the occupying electrons are unpaired electrons. Because the 4f orbital of gadolinium is occupied by 7 unpaired electrons in this manner, the magnetic moment of gadolinium is the maximum as a 4f element.

In the present embodiment, by including gadolinium in the glass contained in the dental polymerizable composition including the (meth)acrylate compound, the X-ray impermeability (the property of blocking X-rays without transmitting them when X-rays are projected) is increased. Thereby, in the present embodiment, the X-ray contrast of the dental polymerizable composition is enhanced.

Because the dental polymerizable composition contains the glass including gadolinium as described above, it is not necessary to separately contain barium glass in the dental polymerizable composition, or, even when barium glass is contained in the dental polymerizable composition, the content of barium glass is reduced. In the present embodiment, it is possible to prevent the dental polymerizable composition from becoming hard. Thus, it is possible to enhance the X-ray contrast while preventing deterioration of operability.

The content of gadolinium in the glass is not particularly limited. For example, when converted into the amount of oxide, the content of gadolinium oxide ($Gd_2O_3$) is 1% by mass or more and 50% by mass or less, preferably 3% by mass or more and 40% by mass or less, and further preferably 5% by mass or more and 30% by mass or less.

When the content of $Gd_2O_3$ in the glass is 1% by mass or more, the X-ray impermeability is increased, and the X-ray contrast is enhanced. When the content of $Gd_2O_3$ in the glass is 50% by mass or less, coloring of the dental polymerizable composition after curing is prevented, and the transparency of the dental polymerizable composition is improved.

The glass contained in the dental polymerizable composition preferably further includes barium. In the present embodiment, by including barium as well as gadolinium in the glass contained in the dental polymerizable composition, high X-ray contrast is exhibited while reducing the content of gadolinium.

In the present embodiment, the glass contained in the dental polymerizable composition includes barium, so that the content of gadolinium is reduced. Accordingly, in the present embodiment, coloring of the dental polymerizable composition after curing is prevented, and the transparency of the dental polymerizable composition is improved.

The content of barium in the glass is not particularly limited. For example, when converted into the amount of oxide, the content of barium oxide (BaO) is 1% by mass or more and 50% by mass or less, preferably 3% by mass or more and 40% by mass or less, and further preferably 5% by mass or more and 30% by mass or less.

When the content of Bao in the glass is 1% by mass or more, the X-ray impermeability is increased and the X-ray contrast is enhanced. When the content of Bao in the glass is 50% by mass or less, coloring of the dental polymerizable composition after curing is prevented, and the transparency of the dental polymerizable composition is improved.

The sum of the content of gadolinium and the content of barium in the glass is not particularly limited. For example, when converted into the amount of oxide, the sum of the content of gadolinium oxide ($Gd_2O_3$) and the content of barium oxide (BaO) is 2% by mass or more and 70% by mass or less, preferably 5% by mass or more and 60% by mass or less, and further preferably 10% by mass or more and 50% by mass or less.

When the sum of the content of $Gd_2O_3$ and the content of Bao is 2% by mass or more, the X-ray impermeability is further increased and the X-ray contrast is further enhanced. When the sum of the content of $Gd_2O_3$ and the content of Bao in the glass is 70% by mass or less, coloring of the dental polymerizable composition after curing is further prevented, and the transparency of the dental polymerizable composition is further improved.

The glass contained in the dental polymerizable composition may include, as other glass components, an alkali metal, aluminum, boron, silicon, and fluorine.

Examples of the alkali metal include lithium, sodium, potassium, and the like. One or two or more alkali metals may be included.

The content of alkali metal in the glass is not particularly limited. For example, when converted into the amount of oxide, the content of lithium oxide ($Li_2O$) and/or sodium oxide ($Na_2O$) and/or potassium oxide ($K_2O$) is 0.001% by mass or more and 10% by mass or less, preferably 0.01% by mass or more and 5% by mass or less, and further preferably 0.1% by mass or more and 1% by mass or less.

When the sum of the content of alkali metal in the glass is 0.001% by mass or more and 10% by mass or less, deterioration of the chemical durability and water resistance of the glass are prevented.

The content of aluminum in the glass is not particularly limited. For example, when converted into the amount of oxide, the content of aluminum oxide ($Al_2O_3$) is 0.1% by mass or more and 30% by mass or less, preferably 0.3% by mass or more and 25% by mass or less, and further preferably 0.5% by mass or more and 20% by mass or less.

When the content of $Al_2O_3$ in the glass is 0.1% by mass or more, the chemical durability and the mechanical strength of the glass is improved, and the stability of the glass in the dental polymerizable composition is increased. When the content of $Al_2O_3$ in the glass is 30% by mass or less, it is possible to prevent the glass from devitrification and deterioration of the acid resistance.

The content of boron in the glass is not particularly limited. For example, when converted into the amount of oxide, the content of boron oxide (B203) is 1% by mass or more and 30% by mass or less, preferably 5% by mass or more and 20% by mass or less, and further preferably 10% by mass or more and 15% by mass or less.

When the content of B203 in the glass is 1% by mass or more, the crystallization stability of the glass is increased. When the content of B203 in the glass is 30% by mass or less, deterioration of the chemical durability and occurrence of non-uniformity of the refractive index of the glass are prevented.

The content of silicon (Si) in the glass is not particularly limited. For example, when converted into the amount of oxide, the content of silicon oxide ($SiO_2$) is preferably 1% by mass or more and 65% by mass or less, more preferably 1% by mass or more and 60% by mass or less, and further preferably 1% by mass or more and 55% by mass or less.

When the content of $SiO_2$ in the glass is 1% by mass or more, it is possible to adjust the viscosity of the dental polymerizable composition containing the glass, and the mechanical strength of the dental polymerizable composition is improved. When the content of $SiO_2$ in the glass is 65% by mass or less, deterioration of the X-ray impermeability of the dental polymerizable composition containing the glass is prevented.

The content of fluorine (F) in the glass is not particularly limited. For example, the content of fluorine is 0.1% by mass or more and 30% by mass or less, preferably 0.3% by mass or more and 20% by mass or less, and further preferably 0.5% by mass or more and 10% by mass or less.

When the content of F in the glass is 0.1% by mass or more and 30% by mass or less, it is possible to easily adjust the viscosity of the dental polymerizable composition containing the glass.

The content of the glass in the dental polymerizable composition is not particularly limited. For example, the content is preferably 40% by mass or more and 90% by mass or less, more preferably 50% by mass or more and 80% by mass or less, and further preferably 60% by mass or more and 70% by mass or less.

When the content of the glass in the dental polymerizable composition is 40% by mass or more, high X-ray contrast is imparted to the dental polymerizable composition containing the glass, and the mechanical strength is improved. When the content of the glass in the dental polymerizable composition is 90% by mass or less, the viscosity of the dental polymerizable composition containing the glass is decreased, and the operability of the dental polymerizable composition is improved.

In the dental polymerizable composition according to the present embodiment, the refractive index nd of the glass contained in the dental polymerizable composition is 1.4 or more and 1.7 or less, preferably 1.45 or more and 1.65 or less, and more preferably 1.5 or more and 1.6 or less. As used herein, the refractive index nd means the refractive index in the D line (a ray having a wavelength of 589 nm).

When the refractive index nd of the glass contained in the dental polymerizable composition is 1.4 or more and 1.7 or less, the difference with the refractive index of the matrix component in the dental polymerizable composition is decreased, and the transparency of the cured product of the resulting dental polymerizable composition is increased.

The form of the glass is preferably powder. When the form of the glass is powder, it is easy to incorporate the glass into the dental polymerizable composition.

The particle diameter of the glass is, in the median diameter, preferably 0.01 μm or more and 20 μm or less, more preferably 0.05 μm or more and 10 μm or less, and further preferably 0.1 μm or more and 1 μm or less. The particle diameter means the average particle diameter defined by the median diameter.

When the particle diameter of the glass is 0.01 μm or more, the operability of the dental polymerizable composition is improved when the glass powder is used for the dental polymerizable composition. When the particle diameter of the glass is 20 μm or less, the abrasion resistance of the cured product of the dental polymerizable composition is improved.

The dental polymerizable composition of the present embodiment preferably includes an inorganic filler. The inorganic filler is a filler containing inorganic components except gadolinium.

The component of the inorganic filler is not particularly limited. For example, the component of the inorganic filler is colloidal silica, hydrophobized particulate silica, aluminum oxide (excluding aluminum oxide in the glass), fluoroaluminosilicate glass, barium glass, and the like. The inorganic filler may be used alone, or two or more inorganic fillers may be used in combination.

The content of the inorganic filler in the dental polymerizable composition is, for example, preferably 0.01% by mass or more and 30% by mass or less, more preferably 0.05% by mass or more and 20% by mass or less, and further preferably 0.1% by mass or more and 10% by mass or less.

When the content of the inorganic filler in the dental polymerizable composition is 0.01% by mass or more, the viscosity of the dental polymerizable composition containing the glass is increased, and the operability of the dental polymerizable composition is improved. When the content of the inorganic filler in the dental polymerizable composition is 30% by mass or less, high operability of the dental polymerizable composition is exhibited while the viscosity of the dental polymerizable composition containing the glass does not become too high.

The dental polymerizable composition according to the present embodiment may include other components, as long as the object of the present invention is not impaired. The other components included in the dental polymerizable composition are, for example, chemical polymerization initiators, photopolymerization initiators, and polymerization inhibitors.

The chemical polymerization initiator is not particularly limited. For example, as the chemical polymerization initiator, a thiourea derivative, a vanadium compound, a tertiary amine, and an organic peroxide can be used.

Among the chemical polymerization initiators, the thiourea derivative functions as a reducing agent.

The thiourea derivative is not particularly limited. Examples of the thiourea derivative include ethylene thiourea, N-methylthiourea, N-ethylthiourea, N-propylthiourea, N-butylthiourea, N-laurylthiourea, N-phenylthiourea, N-cyclohexylthiourea, N, N-dimethylthiourea, N, N-diethylthiourea, N, N-dipropylthiourea, N, N-dibutylthiourea, N, N-dilaurylthiourea, N, N-diphenylthiourea, N, N-dicyclohexylthiourea, trimethylthiourea, tetramethylthiourea, N-acetylthiourea, N-benzoylthiourea, 1-allyl-3-(2-hydroxyethyl)-2-thiourea, 1-(2-tetrahydrofurfuryl)-2-thiourea, N-tert-butyl-N'-isopropylthiourea, 2-pyridylthiourea, and the like.

The thiourea derivative may be used alone, or two or more thiourea derivatives may be used in combination. Among these, N-benzoyl thiourea is preferable in terms of improving the curability of the dental polymerizable composition.

The content of the thiourea derivative in the dental polymerizable composition is not particularly limited. For example, the content is preferably 0.1% by mass or more and 5% by mass or less, more preferably 0.1% by mass or more and 3% by mass or less, and further preferably 0.1% by mass or more and 1% by mass or less. When the content of the thiourea derivative in the dental polymerizable composition is 0.1% by mass or more, the curability of the dental polymerizable composition is further improved. When the content is 5% by mass or less, the solubility of the thiourea derivative in the (meth)acrylate in the dental polymerizable composition is improved.

Among the chemical polymerization initiators, the vanadium compound functions as a reducing agent.

The vanadium compound is not particularly limited. Examples of the vanadium compound include oxovanadium oxalate, vanadyl acetylacetonate, vanadium acetylacetonate, vanadyl stearate, vanadium naphthenate, vanadium benzoyl acetonate, and the like.

The vanadium compound may be used alone, or two or more vanadium compounds may be used in combination. Among these, vanadyl acetylacetonate is preferable in terms of curability of the dental polymerizable composition.

The content of the vanadium compound in the dental polymerizable composition is not particularly limited. The content is preferably 0.001% by mass or more and 5% by mass or less, more preferably 0.0015% by mass or more and 1% by mass or less, and further preferably 0.002% by mass or more and 0.1% by mass or less.

When the content of the vanadium compound in the dental polymerizable composition is 0.001% by mass or more, the curability of the dental polymerizable composition is further improved. When the content of the vanadium compound is 5% by mass or less, the storage stability of the dental polymerizable composition is further improved.

Among the chemical polymerization initiators, the tertiary amine functions as a reducing agent.

The tertiary amine is not particularly limited. Examples of the tertiary amine include a tertiary aliphatic amine and a tertiary aromatic amine.

Examples of the tertiary aliphatic amine include N, N-dimethylaminoethylmethacrylate, triethanolamine, and the like.

Examples of the tertiary aromatic amine include alkyl p-dialkylaminobenzoate, 7-dimethylamino-4-methylcoumarin, N, N-dimethylaniline, N, N-dibenzylaniline, N, N-dimethyl-p-toluidine, N, N-diethyl-p-toluidine, N, N-bis(2-hydroxyethyl)-p-toluidine, N, N, 2,4,6-pentamethylaniline, N, N, 2,4-tetramethylaniline, N, N-diethyl-2,4,6-trimethylaniline, and the like.

Among these, the tertiary amine is preferably the tertiary aromatic amine, and more preferably alkyl p-dialkylaminobenzoate.

Examples of the alkyl p-dialkylaminobenzoate include methyl p-dimethylaminobenzoate, ethyl p-dimethylaminobenzoate, propyl p-dimethylaminobenzoate, amyl p-dimethylaminobenzoate, isoamyl p-dimethylaminobenzoate, ethyl p-diethylaminobenzoate, propyl p-diethylaminobenzoate, and the like.

The tertiary amine may be used alone, or two or more tertiary amines may be used in combination.

Among the chemical polymerization initiators, the organic peroxide functions as an oxidizing agent.

Examples of the organic peroxide include benzoyl peroxide, cumene hydroperoxide, t-butyl hydroperoxide, t-amyl hydroperoxide, 1,1,3,3-tetramethylbutyl hydroperoxide, 2,5-dimethyl-2,5-di(hydroperoxy) hexane, p-diisopropylbenzene monohydroperoxide, p-methane hydroperoxide, pinane hydroperoxide, and the like.

The organic peroxide may be used alone, or two or more organic peroxides may be used in combination. Among these, cumene hydroperoxide is preferable in terms of the curability of the dental polymerizable composition.

The content of the organic peroxide in the dental polymerizable composition is not particularly limited. For example, the content is preferably 0.01% by mass or more and 10% by mass or less, more preferably 0.05% by mass or more and 5% by mass or less, and further preferably 0.1% by mass or more and 3% by mass or less. When the content of the organic peroxide in the dental polymerizable composition is 0.01% by mass or more, the curability of the dental polymerizable composition is further improved. When the content is 10% by mass or less, the open time of the dental polymerizable composition is further increased.

The photopolymerization initiator is not particularly limited. Examples of the photopolymerization initiator include camphorquinone, phenylbis(2,4,6-trimethylbenzoyl) phosphine oxide, 2,4,6-trimethylbenzoyl diphenylphosphine oxide, benzyl ketal, diacetyl ketal, benzyl dimethyl ketal, benzyl diethyl ketal, benzyl bis(2-methoxyethyl) ketal, 4,4'-dimethyl(benzyl dimethyl ketal), anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10,10-dioxide, thioxanthone-10-oxide, benzoin methyl ether, benzoin ethyl ether, benzoin isopropyl ether, benzoin isobutyl ether, benzophenone, bis(4-dimethylaminophenyl) ketone, 4,4'-bis(diethylamino)benzophenone, and the like.

The photopolymerization initiator may be used alone, or two or more photopolymerization initiators may be used in combination. Among these, camphorquinone and phenylbis (2,4,6-trimethylbenzoyl) phosphine oxide are preferable in terms of improving the curability of the dental polymerizable composition.

The content of the photopolymerization initiator in the dental polymerizable composition is not particularly limited. For example, the content is preferably 0.001% by mass or more and 1% by mass or less, more preferably 0.005% by mass or more and 0.5% by mass or less, and further preferably 0.01% by mass or more and 0.3% by mass or less.

When the content of the photopolymerization initiator in the dental polymerizable composition is 0.001% by mass or more, the curability of the dental polymerizable composition is further improved. When the content of the photopolymerization initiator is 1% by mass or less, the storage stability of the dental polymerizable composition is further improved.

Examples of the polymerization inhibitor include dibutyl hydroxytoluene (2,6-di-tert-butyl-p-cresol), 6-tert-butyl-2, 4-xylenol, and the like.

The polymerization inhibitor may be used alone, or two or more photopolymerization initiators may be used in combination. Among these, dibutyl hydroxytoluene is preferable in terms of improving the curability of the dental polymerizable composition.

The content of the polymerization inhibitor in the dental polymerizable composition is not particularly limited. For example, the content is preferably 0.001% by mass or more and 5% by mass or less, more preferably 0.005% by mass or more and 1% by mass or less, and further preferably 0.01% by mass or more and 0.1% by mass or less. When the content of the polymerization inhibitor in the dental polymerizable composition is 0.001% by mass or more and 5% by mass or less, the storage stability of the dental polymerizable composition is improved.

The X-ray contrast after polymerization curing of the dental polymerizable composition according to the present embodiment is 200% or more, preferably 250% or more, and more preferably higher than 300%, compared to that of aluminum. As used herein, the X-ray contrast refers to the X-ray contrast measured by the test method for X-ray contrast of materials for dentistry in accordance with ISO 13116.

In the present embodiment, the X-ray contrast after polymerization curing is 200% or more compared to that of aluminum. Thus, the dental polymerizable composition having high X-ray contrast can be provided.

A formulation of the dental polymerizable composition is not particularly limited. The formulation may be, for example, a two-part formulation including a first agent and a second agent, or a one-part formulation including only a first agent.

In the present embodiment, when the dental polymerizable composition is provided as the two-part formulation, the (meth)acrylate compound described above and the glass including gadolinium described above may be used in either the first agent or the second agent or both.

The glass included in either the first agent or the second agent or both of the two-part formulation may contain barium described above. The glass included in either the first agent or the second agent or both may contain the inorganic filler described above.

As the (meth)acrylate compound included in either the first agent or the second agent or both of the two-part formulation, the (meth)acrylate having no acid group described above may be used. In the (meth)acrylate compound included in the second agent of the two-part formulation, the (meth)acrylate having an acid group described above may further be included.

The first agent of the two-part formulation may include the tertiary amine described above as the chemical polymerization initiator, the photopolymerization initiator described above, and the polymerization inhibitor described above. In the one-part formulation, the organic peroxide may be included as the chemical polymerization initiator.

The property of the first agent and the second agent of the two-part formulation may be, for example, paste and the like.

The mass ratio of the first agent and the second agent of the dental polymerizable composition according to the present embodiment is typically from 10:1 to 1:10, preferably from 1:5 to 5:1.

In the dental polymerizable composition according to the present embodiment, the first agent and the second agent of the two-part formulation may be kneaded and used.

In the present embodiment, as described above, when the dental polymerizable composition is provided as the two-part formulation that includes the first agent and the second agent, because the glass contained in the dental polymerizable composition including the (meth)acrylate compound includes gadolinium, the X-ray impermeability is increased. Therefore, in the present embodiment, even when the dental polymerizable composition is provided as the two-part formulation, the X-ray contrast is enhanced.

Because the dental polymerizable composition contains the glass including gadolinium as described above, it is not necessary to separately contain barium glass in the dental polymerizable composition, or, even when barium glass is contained in the dental polymerizable composition, the content of barium glass is reduced. In the present embodiment, even when the dental polymerizable composition is provided as the two-part formulation including the first agent and the second agent, it is possible to prevent the dental polymerizable composition from becoming hard. Thus, it is possible to enhance the X-ray contrast while preventing deterioration of operability.

In the present embodiment, when the dental polymerizable composition is provided as the one-part formulation that includes only the first agent, the (meth)acrylate compound described above and the glass including gadolinium described above may be used.

The glass included in the one-part formulation may contain barium described above. The glass included in the one-part formulation may contain the inorganic filler described above.

As the (meth)acrylate compound included in the one-part formulation, the (meth)acrylate having no acid group described above may be used.

The one-part formulation may include the thiourea derivative described above as the chemical polymerization initiator, the vanadium compound, the tertiary amine, the photopolymerization initiator described above, and the polymerization inhibitor described above.

The property of the one-part formulation may be, for example, paste and the like.

In the present embodiment, as described above, when the dental polymerizable composition is provided as the one-part formulation, because the glass contained in the dental polymerizable composition including the (meth)acrylate compound includes gadolinium, the X-ray impermeability is increased. Therefore, in the present embodiment, even when the dental polymerizable composition is provided as the one-part formulation, the X-ray contrast is enhanced.

The use of the dental polymerizable composition according to the present embodiment is not particularly limited. The dental polymerizable composition according to the present embodiment may be used, for example, in a variety of dental materials. Examples of the dental materials include dental cements, dental adhesives, dental temporary sealants, dental primers, dental coatings, dental composite resins, dental hard resins, dental cutting resins, dental temporary restoration materials, dental fillers, dentifrices, and the like. Among these, the dental polymerizable composition according to the present embodiment is preferably used for dental cements.

EXAMPLE

Hereinafter, the present invention will be further described with reference to examples. Unless otherwise noted, the numerical value without units and the numerical value with "%" are values in mass standard (% by mass).

<Preparation of Glass>

Glasses having the composition described in Table 1 (Glasses 1 to 3) were prepared. Glasses 1 to 3 were obtained, by pulverizing each glass, as glass powders having a median diameter (average particle diameter) of 0.4 μm. The refractive indices of the obtained glass powders (Glasses 1 to 3) were measured. The average particle diameters and the refractive indices of Glasses 1 to 3 are described in Table 1.

TABLE 1

| GLASS | | 1 | 2 | 3 |
|---|---|---|---|---|
| COMPOSITION | $B_2O_3$ | 10.0 | 10.0 | 10.0 |
| [% BY MASS] | F | 1.0 | 1.0 | 1.0 |
| | $Na_2O$ | 0.1 | 0.2 | 0.2 |
| | $Al_2O_3$ | 10.0 | 9.0 | 8.0 |
| | $SiO_2$ | 44.9 | 41.8 | 39.8 |
| | BaO | 27.0 | 24.0 | 21.0 |
| | $Gd_2O_3$ | 7.0 | 14.0 | 20.0 |
| | TOTAL | 100 | 100 | 100 |
| AVERAGE PARTICLE DIAMETER [μm] | | 0.4 | 0.4 | 0.4 |
| REFRACTIVE INDEX | | 1.54 | 1.55 | 1.56 |

Examples 1 to 7, Comparative Examples 1 and 2

(Preparation of Paste 1)

Paste 1 (a first agent) was obtained by mixing methacrylate having no acid group, a vanadium compound, a thiourea derivative, a filler, a tertiary amine, a photopolymerization initiator, and a polymerization inhibitor in the composition (% by mass) described in Table 2. The filler blended in Paste 1 includes Glasses 1 to 3 and inorganic fillers other than glass (Preparation of Paste 2)

Paste 2 (a second agent) was obtained by mixing methacrylate having no acid group, methacrylate having an acid group, an organic peroxide, a filler, and a polymerization inhibitor in the composition (% by mass) described in Table 2. The filler blended in Paste 2 includes Glasses 1 to 3 and inorganic fillers other than glass.

TABLE 2

| | | | EXAMPLE | | | | |
|---|---|---|---|---|---|---|---|
| | | | 1 | 2 | 3 | 4 | 5 |
| FIRST AGENT | (METH)ACRYLATE HAVING NO ACID GROUP | Bis-GMA | 3.5 | 3.5 | 3.5 | 3.5 | |
| | | UDMA | 17.5 | 17.5 | 17.5 | 17.5 | 15.3 |
| | | EBDMA | 7.0 | 7.0 | 7.0 | 7.0 | |
| | | GDMA | 7.0 | 7.0 | 7.0 | 7.0 | 15.3 |
| | VANADIUM COMPOUND | VAA | 0.03 | 0.03 | 0.03 | 0.03 | |
| | THIOUREA DERIVATIVE | NBTU | 0.7 | 0.7 | 0.7 | 0.7 | 0.3 |
| | FILLER | GLASS 1 | 63.1 | 63.1 | | | 63.0 |
| | | GLASS 2 | | | 63.1 | | |
| | | GLASS 3 | | | | 63.1 | |
| | | BARIUM GLASS | | | | | |
| | | FLUOROALUMINOSILICATE GLASS | | | | | |
| | | FUMED SILICA POWDER 1 | 1.0 | 1.0 | 1.0 | 1.0 | |
| | | FUMED SILICA POWDER 2 | | | | | 6.0 |
| | | FUMED SILICA POWDER 3 | | | | | |

TABLE 2-continued

| | | | | | | | |
|---|---|---|---|---|---|---|---|
| | TERTIARY AMINE | EPA | 0.05 | 0.05 | 0.05 | 0.05 | 0.09 |
| | PHOTOPOLYMERIZATION | CQ | 0.1 | 0.1 | 0.1 | 0.1 | 0.06 |
| | INITIATOR | TPO | | | | | 0.03 |
| | POLYMERIZATION INHIBITOR | BHT | 0.02 | 0.02 | 0.02 | 0.02 | 0.03 |
| | TOTAL | | 100 | 100 | 100 | 100 | 100 |
| SECOND AGENT | (METH)ACRYLATE HAVING NO ACID GROUP | UDMA | 19.8 | 19.8 | 19.8 | 19.8 | 37.4 |
| | | EBDMA | 6.6 | 6.6 | 6.6 | 6.6 | |
| | | GDMA | 6.6 | 6.6 | 6.6 | 6.6 | 7.2 |
| | (METH)ACRYLATE HAVING ACID GROUP | HOMS | 0.3 | | 0.3 | 0.3 | |
| | | MDP | | | | | 3.4 |
| | ORGANIC PEROXIDE | CHP | 2.0 | 2.0 | 2.0 | 2.0 | 0.6 |
| | FILLER | GLASS 1 | 63.6 | 64.0 | | | |
| | | GLASS 2 | | | 63.6 | | |
| | | GLASS 3 | | | | 63.6 | |
| | | BARIUM GLASS | | | | | |
| | | SILICA POWDER | | | | | 44.3 |
| | | FUMED SILICA POWDER 1 | 1.0 | 1.0 | 1.0 | 1.0 | |
| | | FUMED SILICA POWDER 2 | | | | | 7.0 |
| | POLYMERIZATION INHIBITOR | BHT | 0.03 | 0.03 | 0.03 | 0.03 | 0.05 |
| | TOTAL | | 100 | 100 | 100 | 100 | 100 |
| OPERABILITY | EXTRUSION HARDNESS [kgf] | | 5.3 | 5.3 | 5.3 | 5.3 | 4.2 |
| | EVALUATION | | GOOD | GOOD | GOOD | GOOD | GOOD |
| X-RAY | X-RAY CONTRAST [Al %] | | 345 | 345 | 415 | 485 | 210 |
| | EVALUATION | | EXCELLENT | EXCELLENT | EXCELLENT | EXCELLENT | GOOD |

| | | | | EXAMPLE | | COMPARATIVE EXAMPLE | |
|---|---|---|---|---|---|---|---|
| | | | | 6 | 7 | 1 | 2 |
| FIRST AGENT | (METH)ACRYLATE HAVING NO ACID GROUP | Bis-GMA | | | | 3.0 | |
| | | UDMA | | 15.3 | 6.2 | 15.0 | 15.3 |
| | | EBDMA | | | 21.6 | 6.0 | |
| | | GDMA | | 15.3 | 3.1 | 6.0 | 15.3 |
| | VANADIUM COMPOUND | VAA | | | | 0.02 | |
| | THIOUREA DERIVATIVE | NBTU | | 0.3 | | 0.6 | 0.3 |
| | FILLER | GLASS 1 | | | 67.1 | | |
| | | GLASS 2 | | | | | |
| | | GLASS 3 | | 63.0 | | | |
| | | BARIUM GLASS | | | | 68.2 | |
| | | FLUOROALUMINOSILICATE GLASS | | | | | 63.0 |
| | | FUMED SILICA POWDER 1 | | | | 1.0 | |
| | | FUMED SILICA POWDER 2 | | 6.0 | | | 6.0 |
| | | FUMED SILICA POWDER 3 | | | 1.5 | | |
| | TERTIARY AMINE | EPA | | 0.09 | 0.3 | 0.05 | 0.09 |
| | PHOTOPOLYMERIZATION | CQ | | 0.06 | 0.15 | 0.1 | 0.06 |
| | INITIATOR | TPO | | 0.03 | 0.03 | | 0.03 |
| | POLYMERIZATION INHIBITOR | BHT | | 0.03 | 0.09 | 0.02 | 0.03 |
| | TOTAL | | | 100 | 100 | 100 | 100 |
| SECOND AGENT | (METH)ACRYLATE HAVING NO ACID GROUP | UDMA | | 37.4 | | 17.4 | 37.4 |
| | | EBDMA | | | | 5.0 | |
| | | GDMA | | 7.2 | | 5.8 | 7.2 |
| | (METH)ACRYLATE HAVING ACID GROUP | HOMS | | | | 0.3 | |
| | | MDP | | 3.4 | | | 3.4 |
| | ORGANIC PEROXIDE | CHP | | 0.6 | | 2.0 | 0.6 |
| | FILLER | GLASS 1 | | | | | |
| | | GLASS 2 | | | | | |
| | | GLASS 3 | | | | | |
| | | BARIUM GLASS | | | | 68.5 | |
| | | SILICA POWDER | | 44.3 | | | 44.3 |
| | | FUMED SILICA POWDER 1 | | | | 1.0 | |
| | | FUMED SILICA POWDER 2 | | 7.0 | | | 7.0 |
| | POLYMERIZATION INHIBITOR | BHT | | 0.05 | | 0.03 | 0.05 |
| | TOTAL | | | 100 | 0.00 | 100 | 100 |
| OPERABILITY | EXTRUSION HARDNESS [kgf] | | | 4.2 | 3.8 | 6.0 | 4.4 |
| | EVALUATION | | | GOOD | GOOD | POOR | GOOD |
| X-RAY | X-RAY CONTRAST [Al %] | | | 260 | 350 | 300 | 135 |
| | EVALUATION | | | GOOD | EXCELLENT | GOOD | POOR |

The meanings of abbreviations in Table 2 are as follows.

Bis-GMA: 2,2-bis [4-(3-methacryloyloxy-2-hydroxypropyl)phenyl]propane

UDMA: di-2-methacryloyloxyethyl-2,2,4-trimethylhexamethylene dicarbamate

EBDMA: ethylene glycol dimethacrylate

GDMA: 2-hydroxy-1,3-dimethacryloyloxypropane

VAA: vanadyl acetylacetonate

NBTU: N-benzoyl thiourea

Barium glass: barium glass particles with a median diameter (average particle diameter) of 0.4 μm (manufactured by Schott, Inc., G018-053)

Fluoroaluminosilicate glass: fluoroaluminosilicate glass powder with a median diameter (average particle diameter) of 2.2 μm Fumed silica powder 1: Aerosil (registered trade mark) RX300 (hydrophobic fumed silica) (manufactured by Nippon Aerosil Co., Ltd.)

Fumed silica powder 2: Aerosil (registered trade mark) R812 (hydrophobic fumed silica) (manufactured by Nippon Aerosil Co., Ltd.)

Fumed silica powder 2: Aerosil (registered trade mark) R972 (hydrophobic fumed silica) (manufactured by Nippon Aerosil Co., Ltd.)

EPA: ethyl p-dimethylaminobenzoate

CQ: camphorquinone

TPO: phenylbis(2,4,6-trimethylbenzoyl) phosphine oxide

BHT: dibutyl hydroxytoluene

HOMS: 2-methacryloyloxyethyl succinic acid

MDP: 10-methacryloyloxydecyldihydrogenphosphate

CHP: cumene hydroperoxide

<Fluoroaluminosilicate Glass Powder>

A batch was obtained by sufficiently mixing and stirring 22 g of aluminum oxide, 23 g of anhydrous silicic acid, 12 g of calcium fluoride, 15 g of calcium phosphate, and 28 g of strontium fluoride in a mortar. The batch was placed in a porcelain crucible, heated in an electric furnace to 1200° C. at a temperature rising rate of about 7° C./minute, and kept for 3 hours. The melt liquid was poured into water to obtain a quench glass. The quench glass was crushed to obtain a fluoroaluminosilicate glass powder. The median diameter (average particle diameter) of the inorganic powder was 2.2 μm.

Next, Paste 1 and Paste 2 were mixed in Examples 1 to 6 and Comparative Examples 1 and 2, and only Paste 1 was mixed in Example 7, and operability was evaluated.

<Operability>

A syringe (5 mL system cartridge) (manufactured by Sulzer Mixpac AG, SDL X05-01-78) was filled with Paste 1 and Paste 2, or filled with only Paste 1. To the syringe, a mixing tip (manufactured by Sulzer Mixpac AG, Helical S-type, ML 2.5-08-S) (2.5 mm in inside diameter, 39.7 mm in length, and 0.19 ml in volume) was attached. The ratio (volume ratio) of the first agent to the second agent was 1:1 in Examples 1 to 4 and Comparative Example 1, and 3:2 in Examples 5 to 6 and Comparative Example 2. The syringe was set on a jig, compressed using an universal test machine, and measured. The crosshead speed was 10 mm/min. The maximum point test force was determined as the extrusion hardness (kgf). The evaluation criteria for operability are as follows. The results of measurement and evaluation are described in Table 2.

Good: extrusion hardness was less than 5.5 kgf

Poor: extrusion hardness was 5.5 kgf or more

Next, X-ray contrast was evaluated for the cured product obtained by polymerizing and curing Paste 1 and Paste 2 mixed in Examples 1 to 6 and Comparative Examples 1 and 2, and the cured product obtained by polymerizing and curing only Paste 1 mixed in Example 7.

<X-Ray Contrast>

A circular jig (15 mm diameter, 1 mm thick) was filled with a paste, and the paste was cured using a light irradiator. The obtained cured product was X-ray-photographed and the X-ray contrast was evaluated by calculating the percentage with comparison to that of aluminum, following the test method for X-ray contrast of materials for dentistry in accordance with ISO 13116. The evaluation criteria for X-ray contrast are as follows. The results of measurement and evaluation are described in Table 2.

Excellent: More than 300% compared to aluminum

Good: 200% or more and 300% or less compared to aluminum

Poor: less than 200% compared to aluminum

From Table 2, in the dental polymerizable compositions (Examples 1 to 7) including a (meth)acrylate compound and a glass including gadolinium, both operability and X-ray contrast were favorable.

In contrast, in the dental polymerizable compositions (Comparative Examples 1 and 2) that do not include a glass including gadolinium, at least operability or X-ray contrast was poor.

While embodiments of the invention have been described, the invention is not limited to specific embodiments, and various modifications and variations are possible within the scope of the invention as claimed.

The present application is based on and claims priority to Japanese Patent Application No. 2021-062368, filed Mar. 31, 2021, the contents of which are incorporated herein by reference in their entirety.

The invention claimed is:

1. A dental polymerizable composition comprising:
a (meth)acrylate compound; and
a glass;
wherein the glass includes gadolinium and barium, and
wherein a content of gadolinium in the glass, when converted into an amount of oxide, is 3% by mass or more and 40% by mass or less, and a content of barium in the glass, when converted into an amount of oxide, is 1% by mass or more and 50% by mass or less.

2. The dental polymerizable composition according to claim 1, further comprising an inorganic filler.

3. The dental polymerizable composition according to claim 1, wherein a refractive index nd of the glass is 1.4 or more and 1.7 or less.

4. The dental polymerizable composition according to claim 1, wherein an X-ray contrast after polymerization curing of the dental polymerizable composition is 200% or more compared to the X-ray contrast of aluminum.

5. The dental polymerizable composition according to claim 1, wherein a formulation of the dental polymerizable composition is provided as a two-part formulation including a first agent and a second agent.

6. The dental polymerizable composition according to claim 1, wherein a formulation of the dental polymerizable composition is provided as a one-part formulation.

* * * * *